United States Patent
Kincaid et al.

(10) Patent No.: US 6,207,074 B1
(45) Date of Patent: *Mar. 27, 2001

(54) QUICK RELEASE OF CHLORINE FROM TRICHLOROISOCYANURIC ACID

(75) Inventors: Thomas R. Kincaid, Reno, NE (US); Dana W. Somesla, Riverside, CA (US)

(73) Assignee: Chem Lab Products, Inc., Ontario, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/021,000

(22) Filed: Feb. 9, 1998

(51) Int. Cl.$^7$ .............. C01B 11/00; A62D 3/00; C09K 3/00
(52) U.S. Cl. .............. 252/187.34; 252/186.1; 252/186.25
(58) Field of Search .............. 252/186.1, 187.1, 252/187.33, 187.34, 186.25, 186.34, 186.35; 210/753, 754, 755

(56) References Cited

U.S. PATENT DOCUMENTS

| | | | | |
|---|---|---|---|---|
| 3,361,675 | * | 1/1968 | Fuchs et al. | 510/381 |
| 4,115,270 | * | 9/1978 | Phillips | 210/169 |
| 4,193,888 | * | 3/1980 | McHugh | 252/99 |
| 4,279,764 | * | 7/1981 | Brubaker | 252/99 |
| 4,557,926 | * | 12/1985 | Nelson et al. | 424/19 |
| 4,863,632 | * | 9/1989 | Aronson et al. | 252/186.35 |
| 4,954,316 | * | 9/1990 | Globus | 422/37 |
| 5,055,219 | * | 10/1991 | Smith | 252/102 |
| 5,114,647 | * | 5/1992 | Levesque et al. | 264/115 |
| 5,128,342 | * | 7/1992 | Globus | 514/241 |
| 5,674,429 | * | 10/1997 | Lachocki et al. | 252/186.28 |

* cited by examiner

*Primary Examiner*—Jan Ludlow
*Assistant Examiner*—LaToya Cross
(74) *Attorney, Agent, or Firm*—Donald D. Mon

(57) ABSTRACT

A mixture consisting essentially of dry trichloroisocyanuric acid, dry surfactant particles, and bulking agents is disclosed. The mixture serves as a quickly dissolving chlorine release mixture used in shock treatment of substantial bodies of water. The surfactant is provided to wet the trichloroisocyanuric acid particles and facilitate their quick solution into the water.

4 Claims, No Drawings

US 6,207,074 B1

QUICK RELEASE OF CHLORINE FROM TRICHLOROISOCYANURIC ACID

FIELD OF THE INVENTION

This invention relates to the "shock" treatment of substantial bodies of water with chlorine quickly released from trichloroisocyanuric acid. Trichloroisocyanuric acid is ordinarily very slow to dissolve and to release its chlorine.

BACKGROUND OF THE INVENTION

Substantial bodies of water such as swimming pools, spas, and cooling towers require constant attention to the elimination of undesirable organic material such as waste material, organic compounds, algae and bacteria. The infusion of gaseous chlorine or of hypochlorite ion is a conventional way to provide an oxidizing agent for this purpose.

There are two levels of attack. One is for the long term maintenance of an existing agreeable condition, in which the level of the oxidizing agent is kept low, and the substance is supplied at a slow steady rate. Examples are the use of slowly dissolving tablets of the oxidizing agent placed in the body of water or in a recirculating system supplying it, or in a slow but steady stream of an oxidizing substance, such as gaseous chlorine, hypochlorite solution, oxygen, peroxides and ozone.

The other level of attack is when the conditions in the body of water have deteriorated to the point where a slow supply is insufficient to eliminate the problem, and in which a vigorous attack must be made. In such event, a large amount of oxidizing agent is added to the body very quickly, so that the chlorine concentration rises well above that which would be maintained during routine operations. Such a treatment is called a "shock" treatment by persons familiar with this art.

Especially for domestic bodies of water, but also for many other substantial-sized bodies of water such as cooling towers, the amount of chemicals needed for a shock treatment is relatively small in weight and bulk, and would most conveniently be provided in small containers or pouches. These must be packaged to have a reasonable shelf life, and be agreeable when the package is opened. The best situation would be if the product were safe to store and handle as well as easy to use.

There are many products which from a chemistry standpoint can be used for shock treatment. Aqueous hypochlorite solutions are a familiar example. A pervasive problem is the bulk which must be handled, and the rapid loss of chlorine. Sources of treatment gas such as chlorine and ozone require capital installations and handling of hazardous materials.

In contrast, trichloro compounds would be preferable because of their substantial chlorine content, safety in handling and convenience. Still they are slow to dissolve.

This property of slow dissolving is ideal for long-term maintenance, and is the principal reason why trichloroisocyanuric acid (hereinafter called "trichloro") is so frequently used in compressed tablets kept submerged in a swimming pool or in a feeder. The trichloro in a tablet form will dissolve very slowly, and will maintain a steady, slow chlorine release for a long period of time when that characteristic is desirable. However, its slow dissolving rate, even in finely divided form, is a contraindication against its use for shock treatment because immediate chlorine release is the objective. An additional complication occurs because trichloro when finely grained simply floats and coagulates on the surface of the water for a long period of time, and when finally wetted, the clusters sink to the bottom where they dissolves slowly.

Trichloro has a substantial advantage in its stability while dry, and in its low flammability. Except for the fact that unassisted it is useless for a shock compound, it would be an ideal domestic source of chlorine for this application.

In contrast, dichloroisocyanurate (hereinafter called "dichloro") is readily soluble, and is used for shock treatments. Its disadvantages compared to other chlorine compounds include, but are not limited to a higher price, lower relative available chlorine and the potential fire hazard of the anhydrous form. Its only comparative advantage is its speed of solution into water, which is rapid. For this reason it is used for shock treatments despite its disadvantages.

This situation has not gone unnoticed, and efforts have been made to provide mixtures of trichloro and other chemicals, which provide pathways by which the chlorine in trichloro can quickly be released. These arrangements have brought with them a number of problems, because characteristically they include substances which will react with trichloro to reduce it to the more soluble dichloro when in the water, or which provide other reaction paths involving reactants that must be stored together with the trichloro so as to be available for the intended reaction. Accordingly, when used, trichloro has generally been accompanied by substances which bring their own expense and problems. The result of all of this is that trichloro has generally been disfavored for use in shock treatment of large bodies of water.

It is an object of this invention to provide a mixture of trichloro and a small amount of another substance to be described which mixture is stable, safe to handle, does not constitute a flammability risk, has a relatively lower toxic risk and which dissolves very quickly.

This composition is intended for use in substantial volumes of water in which the composition will be dissolved in an unbounded but very local region, from which it disperses into the larger volume. It is not intended as a local oxidizer or cleanser for surfaces, or as a solution for direct use on anything, but instead is intended for infusion into the substantial volume very quickly after the trichloro is dissolved, thereby to provide a quick increase in chlorine in the substantial body of water.

There is yet another problem inherent in the use of trichloro. It has so much chlorine content per unit of weight or volume that a small amount of it suffices for a very large body of water. For example, 6 ounces of trichloro will suffice to shock treat a swimming pool containing 12,000 gallons of water, raising its chlorine concentration by about 3 ppm.

The small size of this portion presents the problem of providing to the consumer an amount of the product which can be used at one (1) pound per 12,000 gallons of water (a traditional premium consumer product dosage rate) for shock treatment. Accordingly, a bulking agent may be provided as an inert diluent so a dose can be presented to the consumer in a single package and in a condition such that he can readily transfer it from the package, such as a plastic pouch, to the body of water. In addition the dose delivered is accurate, much more accurate than if a small amount of the trichloro were measured out of a larger container.

The bulking agent is inert relative to the dissolving of the trichloro into the water, and to its release of oxidizing agent. Its purpose is not to assist these functions, but to dilute the trichloro by weight for both dose control and affixing an acceptable price per pound. However if this inert diluent can also provide other advantages such as reduction (or practical elimination) of flammability or to stabilize the active ingredients, or clarify the water (or condition the water) so much the better.

It is an object of this invention to accompany trichloro with a substance which will accelerate its solution without taking part in the chlorine release, and if desired, to provide additives as bulking agents, and other additives which provide other water treatment properties in addition to those provided by the released chlorine, but which take no part in the release of the chlorine or dissolving of the trichloro.

BRIEF DESCRIPTION OF THE INVENTION

This invention consists essentially of a dry mixture of granulated trichloroiscyanuric acid ("trichloro") and a surfactant having the property when placed in water of wetting the trichloro and faciliting its quick solution into the water.

It is essential to this invention that the solution of trichloro be very rapid, and be completed during the time when the local concentration of the surfactant remains high enough adequately to disperse and wet the surface of trichloro granules when it is exposed to water during its immersion and dissolution. The same amount of surfactant dispersed through the entire body of water would not suffice for the purpose. The trichloro would simply stay dry or dissolve very slowly as though the surfactant were not present at all. To provide surfactant in the whole body of water in a concentration sufficient to dissolve the product would be to make the water system foamy and unacceptable for its intended purpose. This is a local action in a limited but unbounded region of a much larger body of water.

According to this invention, the surfactant and the trichloro are dry loose particles that are intimately and physically mixed, but not otherwise pressed or tabletted. A very large exposed area of the trichloro is desired, a result attained by making the particle size small. The mixture is dumped together onto the surface of the water. The surfactant dissolves almost instantly to form a small local unbounded region containing a sufficiently high concentration of surfactant, within which the trichloro is present to dissolve the trichloro. The trichloro is wetted because of the surfactant, and quickly dissolves in the local region. The surfactant remains at an adequate concentration in this region so that as the trichloro particles disperse, their newly exposed surfaces are wetted and dissolved. After dissolution is completed, the surfactant and the dissolved trichloro disperse into the larger body, where the classical release of chlorine occurs. The concentration of surfactant in the body of water is very small in the total body of water, on the order of a 100,000 fold dilution, while the chlorine concentration is increased to an effective level for shock treatment.

It is instructive to observe this event. A packet of this mixture dumped onto the surface of a swimming pool swiftly forms a downwardly and laterally progressing enlarging plume in which the presence of the trichloro as it dissolves and disperses is visually evident. This is the "region". The plume soon disperses, and there is no residual solid trichloro. In a short time, usually much less than a minute, all of the trichloro will have dissolved. There is no visible indication that anything had been added.

DETAILED DESCRIPTION OF THE INVENTION

The source of available chlorine in the mixture according to this invention is trichloro-s-triazine trione, also called trichloroisocyanuric acid ("trichloro" herein). It is the fully chlorinated product obtained from the tri-sodium salt of isocyanuric acid. When dissolved, it reacts with water and releases available chlorine used for oxidizing purposes.

As discussed above, its unassisted rate of solution in water is unacceptably slow for use in shock treatment. The inventors herein have observed that the rate of solution will be accelerated by providing conditions in which a sufficient concentration of a suitable surfactant wets the trichloro, and will keep the surface of the trichloro wet while it dissolves. Obviously this cannot be a pre-wet combination, because when the trichloro is wetted, it immediately begins its decomposition.

There have been described arrangements in which chemical pathways are provided to accelerate the dissolution of trichloro in water. These require the use of a large percentage of a compound which is reactive with the trichloro. This poses the problems of cost, and maintaining the product while in storage in a suitably dry condition.

In order to be available for use when the product is placed in water, it is evident that the surfactant must not react with the trichloro in the packet. Such surfactants appear to be very few in number. For this product, sodium lauroyl sarcosinate is suitable and preferred. It is very soluble, and provided in powder form. Potassium perfluoroalkyl sulfonate may be used instead of, or in combination with it to provide the same relative amount by weight.

In order to assure that there will be a sufficient local and temporary concentration of surfactant to be present while the trichloro is dissolving, the ratio by weight of dry trichloro to dry surfactant should be between about 1300:1 and about 130:1, preferably about 600:1.

Both must be dry and are best present as a mixture of granules or particles so as to minimize any tendency to float on the surface of the water, as might occur if they are too finely powdered, or to sink before dissolving if too large a particle.

For the trichloro, a particle size to pass 20 mesh and 50% to be retained on 200 mesh screen is suitable. The particle size of the surfactant may be about the same, but is less critical because it dissolves so quickly.

This invention is a binary mixture which consists essentially of a dry mixture of trichloro and a suitable non-reactive surfactant. Inert additives, which are inert in the sense that they take no part in the release of chlorine from the trichloro may be added for various other purposes.

The principal use of such additives is as a bulking agent, where a small enough amount of the active ingredients, (trichloro and surfactant) can be presented to the consumer in a larger bulk at a lower cost per pound with significantly reduced chemical hazard. These additives must not themselves be deleterious to the mixture in storage or in the water, nor to the quality of the water. For example they should not cause cloudiness, or leave a residue in the water or on the bottom.

For the above reasons, the additives are preferably soluble and must be stable relative to the rest of the mixture. In a commercially viable product, they should also be inexpensive.

One useful additive for a bulking agent is sodium chloride, which meets all requirements, except that it is slightly hygroscopic, so that great care must be taken during packaging. When it is used, it is better to accompany it with a substance which acts as a desiccant which will preferentially absorb any water, and which can absorb any slight chlorine odor which maybe generated in the package. For this purpose, sodium carbonate is very suitable. It acts as a desiccant and as an odor-collector.

While by its very presence, boric acid acts as a bulking agent, it is included in this formulation for two others of its well-known properties. The first is as a flame retardant, an advantage during handling and storage. The other is to improve flowability of the mixture. This assists in assuring complete mixing, accurate packaging, and ready release from the package.

The amount of surfactant used in this invention is insufficient for any practical use except within the limited region in which it is placed as part of its mixture with the trichloro, and is deliberately made so small that after dispersion its concentration is so trifling that it will not grossly affect the pool conditions.

The mixture according to this invention consists essentially of trichloro and surfactant in the ratio between themselves about 1300 to 130 parts by weight of trichloro to about 1 part by weight of surfactant. The preferred amount of surfactant is that which will provide the minimum concentration of surfactant in the limited region that will result in quick solution of the trichloro. While amounts somewhat greater than this will do no harm to users of the treated water, still it is best to limit the amount of a material which in a sufficient concentration could produce foaming in larger concentrations.

The presently preferred formulation, of which 6 ounces will provide about 3 ppm of chlorine in a 12,000 gallon pool, is as follows:

| | |
|---|---|
| Boric acid, dry powder: | 10% |
| Sodium carbonate, dry powder: | 10% |
| Sodium chloride; dry powder: | 40% |
| Surfactant, sodium lauroyl-sarcosinate dry powder: | 0.015% |
| Trichloro: | balance to 100%, in | which all except the trichloro and surfactant are bulking agents. While only one or two of these bulking agents can be used, the preferred formulation will use all three. Boric acid has the additional optional properties of improving flowability and flame retardancy.

The ratio of bulking agent or agents may vary from this total of 60%, thereby enabling a packet of the same weight to contain more or less of the trichloro. It has been found that if at least a total of about 20% of the above mixture is of these bulking agents, there is a useful control of inadvertent dampness, resulting odor, and some reduction in flammability. Flammability of trichloro is very low to begin with, so that boric acid is optional. There is no upper limit, except that there must be a sufficient amount of the trichloro to provide an advantage. The basic mixture of trichloro and surfactant is fully useful and safe, without bulking agents or additives for other purposes such as odor control, desiccation, or reduction of flammability (while also serving as bulking agents).

This invention is not to be limited by the embodiments described in the description, which are given by way of example and not of limitation, but only in accordance with the scope of the appended claims.

I claim:

1. A quickly dissolving chlorine release mixture for shock treatment of a substantial body of water as the consequence of its rapid dissolution into a localized region of a said body of water and subsequent dispersion into its entire volume, said mixture consisting essentially of:

dry trichloroisocyanuric acid ("trichloro") particles having an exposed surface; and dry water soluble surfactant particles, said trichloro and surfactant particles being intimately and loosely mixed with one another;

said surfactant having the properties of ready solution into the water and wetting of the surface of the trichloro particles, said surfactant being provided in an amount related to the amount of said trichloro sufficient to wet said surfaces while said acid particles and dissolved surfactant are momentarily together in said localized region, and insufficient in amount to adversely affect the water after it becomes dispersed into the entire volume body of water;

said mixture further including an inert water soluble bulking agent mixed into it whereby to provide a more conveniently marketed and dispensed product, said bulking agent in the amounts supplied in the mixture being ineffective to change the rate of solution of the trichloro, or to affect its release of chlorine, or to affect its rate of release of chlorine;

and in which a substance to improve flowability is included in said bulking agent wherein said substance to improve flowability includes at least boric acid.

2. A quickly dissolving chlorine release mixture for shock treatment of a substantial body of water, consisting essentially of, in percentages by weight:

dry trichloroisocyanuric acid ("trichloro") particles: balance to 100% dry sodium lauroyl sarcosinate: 0.015% and, bulking agents ineffective substantially to change the rate of solution of the trichloro or to affect its release or rate of release of chlorine: 60% said bulking agents being the following, in percentages by weight indicated:
Boric acid, dry powder: 10%
Sodium carbonate, dry powder: 10%
Sodium chloride, dry Powder: 40%.

3. A mixture according to claim 2 in which said trichloro particles pass a 20 mesh screen and about 50% are retained on a 200 mesh screen.

4. A mixture according to claim 1 in which the ratio by weight of said acid to said surfactant is less than about 1300:1.

* * * * *